(12) United States Patent
Xu et al.

(10) Patent No.: US 8,361,967 B2
(45) Date of Patent: Jan. 29, 2013

(54) BETA SHEET INHIBITING PEPTIDES FOR PREVENTING AND/OR TREATING ALZHEIMER'S DISEASE

(75) Inventors: Shumei Xu, Tianjin (CN); Genfa Zhou, Tianjin (CN); Wei Wang, Tianjin (CN)

(73) Assignee: Tianjin Medical University, Tianjin (CN)

( * ) Notice: Subject to any disclaimer, the term of this patent is extended or adjusted under 35 U.S.C. 154(b) by 34 days.

(21) Appl. No.: 12/921,693

(22) PCT Filed: Mar. 13, 2008

(86) PCT No.: PCT/CN2008/000497
§ 371 (c)(1),
(2), (4) Date: Dec. 22, 2010

(87) PCT Pub. No.: WO2009/111906
PCT Pub. Date: Sep. 17, 2009

(65) Prior Publication Data
US 2011/0105404 A1    May 5, 2011

(51) Int. Cl.
*A01N 37/18*     (2006.01)
*A61K 38/00*     (2006.01)
*A61K 38/04*     (2006.01)

(52) U.S. Cl. ....... 514/17.8; 514/17.7; 530/300; 530/328

(58) Field of Classification Search .......... None
See application file for complete search history.

(56) References Cited

U.S. PATENT DOCUMENTS

| | | |
|---|---|---|
| 6,022,859 A | 2/2000 | Kiessling et al. |
| 6,582,945 B1 | 6/2003 | Raso |
| 6,905,686 B1 | 6/2005 | Schenk |
| 2006/0079447 A1 | 4/2006 | Wetzel |

FOREIGN PATENT DOCUMENTS
WO     2004087733 A2    10/2004

OTHER PUBLICATIONS

Vickers, Drug Ageing, 2002, 19 (7), pp. 487-494.*
Austen et al., "Designing peptide inhibitors for oligomerization and toxicity of Alzheimer's β-amyloid peptide" Biochemistry, Feb. 19, 2008, vol. 47, pp. 1984-1992.
Chacon et al, "β-sheet breaker peptide prevents β-induced spatial memory impairments with partial reduction of amyloid deposits", Mol. Psychiatry, 2004, vol. 9, No. 10, pp. 953-961.
Jarrett et al., "Seeding "one-dimensional crystallization" of amyloid: a pathogenic mechanism in Alzheimer's disease and scrapie?", Cell, 1993, col. 6, pp. 1055-1058.
Matsouk et al, "Noval therapeutic approach for the treatment of Alzheimer's disease by peripheral administration of agents with an affinity to β-amyloid", J. Neurosci, 2003, vol. 23, No. 1, pp. 1-5.
Soto et al, "Inhibition of Alzheimer's amyloidosis by peptides that prevent β-sheet conformation", Biochem. Biophys. Res. Commun., 1996, vol. 226, No. 3, pp. 672-680.
Tjernberg et al, "A Molecular Model of Alzheimer amyloid β-peptide fibril formation", the Journal of Biological Chemistry, Apr. 20, 1999, vol. 274, No. 18, pp. 12619-12625.
Younkin et al., "Evidence that Aβ42 is the real culprit in Alzheimer's disease", Ann. Neurol., 1995, vol. 37, pp. 287-288.
International Search Report from corresponding PCT Application No. PCT/CN2008/000497, mailed Dec. 25, 2008, with English Translation, 15 pages.
European Supplementary Search Report from corresponding Application No. 08714950.6, mailed Jul. 11, 2011, 3 pages.

* cited by examiner

*Primary Examiner* — Olga N Chernyshev
(74) *Attorney, Agent, or Firm* — Fish & Richardson P.C.

(57) ABSTRACT

Provided are β-sheet breaker peptides binding to β amyloid peptide (Aβ1-42), which have the homologous sequence with Aβ 14-23. β-sheet breaker peptides can be used for the manufacture of a medicament for prophylactic and/or therapeutic treatment of Alzheimer's Disease.

6 Claims, 8 Drawing Sheets

Fig 1A

Date/Time: 2006-06-23, 14:12:26
Data File: D:\GL Biochem\HD-10-1-F-060623.mdy

Analyst: Mei Mei
Date/Time: 2006-06-23, 14:12:36

Sample Description:
Structure   : H101
Column      : 4.6×250mm, Sinochrom ODS-BP-5
Solvent A   : 0.05% trifluoroacetic in 100% acetonitrile
Solvent B   : 0.065% trifluoroacetic in 100% water
Gradient    :           A        B
              0.01min   24%      76%
              25min     54%      46%
              25.1min   100%     0%
              30min            STOP
Flow rate   : 1.0 mL/min
Wavelength  : 220nm

Results

| Peak No. | Peak ID | Ret Time | Height | Area | Conc. |
|---|---|---|---|---|---|
| 1 | | 8.157 | 1185.789 | 18498.605 | 0.8737 |
| 2 | | 10.092 | 1412.681 | 33728.039 | 1.5930 |
| 3 | | 10.490 | 84716.367 | 2018962.250 | 95.3599 |
| 4 | | 11.552 | 2164.159 | 46013.477 | 2.1733 |
| Total | | | 89478.997 | 2117202.371 | 100.0000 |

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1

His Lys Gln Leu Val Phe Phe Glu Glu Asp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 2

His Lys Gln Leu Pro Phe Phe Glu Glu Asp
1               5                   10

<210> SEQ ID NO 3
<211> LENGTH: 10
<212> TYPE: PRT
<213> ORGANISM: Artificial Sequence
```

-continued

```
<220> FEATURE:
<223> OTHER INFORMATION: Chemically Synthesized

<400> SEQUENCE: 3

His Gln Lys Leu Val Phe Phe Ala Glu Asp
 1               5                  10

<210> SEQ ID NO 4
<211> LENGTH: 42
<212> TYPE: PRT
<213> ORGANISM: Homo sapiens

<400> SEQUENCE: 4

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
             20                  25                  30

Gly Leu Met Val Gly Gly Val Val Ile Ala
         35                  40

<210> SEQ ID NO 5
<211> LENGTH: 10
<212> TYPE: PRT
<213> ORGANISM: Artificial Sequence
<220> FEATURE:
<223> OTHER INFORMATION: Chemically Synthesized
<220> FEATURE:
<221> NAME/KEY: VARIANT
<222> LOCATION: (2)...(3)
<223> OTHER INFORMATION: Xaa=Lys or Gln
<220> FEATURE:
<221> NAME/KEY: VARIANT
<222> LOCATION: 5
<223> OTHER INFORMATION: Xaa=Val or Pro
<220> FEATURE:
<221> NAME/KEY: VARIANT
<222> LOCATION: 8
<223> OTHER INFORMATION: Xaa=Ala or Glu

<400> SEQUENCE: 5

His Xaa Xaa Leu Xaa Phe Phe Xaa Glu Asp
 1               5                  10

<210> SEQ ID NO 6
<211> LENGTH: 5
<212> TYPE: PRT
<213> ORGANISM: Homo sapiens

<400> SEQUENCE: 6

Lys Leu Val Phe Phe
 1               5
```

BETA SHEET INHIBITING PEPTIDES FOR PREVENTING AND/OR TREATING ALZHEIMER'S DISEASE

CROSS REFERENCE TO RELATED APPLICATION

This application is the U.S. National Stage Application of International PCT Application No. PCT/CN2008/000497, filed Mar. 13, 2008. The contents of this priority application are hereby incorporated by reference in its entirety.

TECHNICAL FIELD

The present invention relates to polypeptides and use thereof. In particular, the invention relates to a type of β-sheet breaker peptides which can be used for prevention and/or treatment of Alzheimer's Disease, and their use in prevention and/or treatment of Alzheimer's Disease.

BACKGROUND

Alzheimer's Disease (AD), also called senile dementia, is a type of neurodegenerative disease. It has hidden onset and progressive pathology, accompanying typical clinical characteristics of integrated cognitive impairment and personality change. The AD patients will undergo early and recent memory impairment, and subsequently progressive intelligence decline, aphasia, loss of reasoning ability and dyskinesia. This disease will seriously affect the quality of life of the patients and their family members, also incurs a heavy burden on the patient's families and the society.

With the accelerating population aging process, senile diseases have become a significant problems affecting human health. AD, cancer, and cardio- and cerebrovascular accident are three leading causes of mortality in old people. It is believed that AD will be the fourth risk factor to human health in the 21st century. World Health Organization has included AD as one of the five major diseases in 21st century. China entered into aging society in 1999. By the end of 2004, there are 143 million elder people aged 60 and more, comprising 10.97% of the total population. It is predicted that this number will reach 200 million by 2014, 300 million by 2026, and more than 400 million by 2037. The number of elder people will rise to its maximum in 2051 and remains at a scale of 300 million to 400 million. Increasing population of elders leads to increasing incidence of Alzheimer's disease. It is currently reported that more than 20% of people over 80 years are suffered this disease in Europe, Japan and the United States. There are more than 50 million people over 65 years suffered from different types of dementia all over the world.

The main pathological changes of AD are characterized by: extensively and intercellularly formed senile plaque (SP), which results from the deposition of β-amyloid peptide (abbreviated as Aβ or βA); neurofibrillary tangles (NT) resulted from hyperphosphorylated Tau protein in nerve cells; and extensive neuron loss. Lots of evidences indicate that the neurotoxicity of Aβ is the common cause of the diverse etiologies. Therefore, the prevention and/or treatment efforts targeting Aβ have become the focus of AD research in recent years.

Aβ is the metabolite of β-amyloid precursor protein (APP). Under normal conditions, APP generates soluble sAPPα under the enzymatic catalysis of α-secretase. sAPPα have the functions of reducing the concentration of intracellular calcium, regulating synaptic plasticity, promoting synaptic growth and protecting the neuron. This is the main pathway of APP processing, which does not generate Aβ. In the other pathway, APP generates sAPPβ and C99 under the enzymatic catalysis of β-secretase. C99 then releases Aβ peptide under the enzymatic catalysis of γ-secretase. The hydrolysis of C99 by γ-secretase is a heterogeneous process: an enzymatic cleavage between alanine 713 and threonine 714 generates $A\beta_{1-42}$; and an enzymatic cleavage between valine 711 and isoleucine 712 generates $A\beta_{1-40}$ (Selkoe D J. Alzheimer's disease: genes, proteins, and therapy. Physiol Pev, 2001, 81 (2): 741-766). $A\beta_{1-42}$ accounts for about 10% of total Aβ protein, $A\beta_{1-40}$ accounts for about 90%. However, $A\beta_{1-42}$ is more likely to aggregate, and the aggregated $A\beta_{1-42}$ constitutes the basic component of senile plaques.

The primary structure of $A\beta_{1-42}$ peptide is shown as follows (SEQ ID NO:4):

```
Asp-Ala-Glu-Phe-Arg-His-Asp-Ser-Gly-Tyr-Glu-Val-His-His-Gln-
1                   5                   10                  15

Lys-Leu-Val-Phe-Phe-Ala-Glu-Asp-Val-Gly-Ser-Asn-Lys-Gly-Ala-
16                  20                  25                  30

Ile-Ile-Gly-Leu-Met-Val-Gly-Gly-Val-Val-Ile-Ala
31                  35                  40  42
```

Ten amino acid residues on C-terminal of $A\beta_{1-42}$ (residues 33 to 42) and residues 17 to 21 are highly hydrophobic and constitute the hydrophobic region of Aβ1-42; amino acid residues 28-42 have more probability to form a β-sheet conformation, while the amino acid residues 9-21 may also form a β-sheet conformation. B-sheet conformation is conducive to aggregation of $A\beta_{1-42}$ peptide. Experimental results show that three residues on C terminal, $Val^{40}Ile^{41}Ala^{42}$, stabilize the β-sheet conformation and are conducive to formation of a β-sheet. N-terminal of Aβ 1-42 peptide is hydrophilic, and can form conformation of α-helix, random helix or β-sheet, depending on the different solution conditions. It has been shown that the β-sheet conformation is conducive to the aggregation of Aβ peptide, and the aggregation of Aβ peptide is due to the interaction between its hydrophobic regions. Soto et al. (Soto C, Kindy M S, Baumann M, et al., Inhibition of Alzheimer's amyloidosis by peptides that prevent beta-sheet conformation. Biochem. Biophys. Res. Commun. 1996, 226(3):672-680) replaced amino acid residues adjacent to the hydrophobic regions of Aβ peptides by proline, the resulting small peptides will not form a β-sheet conformation, and binds to Aβ peptide instead, allowing to maintain Aβ peptide in its random helical conformation and inhibit its aggregation. It has also been shown that one hydrophobic region of Aβ peptide, a pentapeptide Aβ16-20 (Lys-Leu-Val-Phe-Phe (SEQ ID NO:6)), can binds to Aβ peptide and thus prevent aggregation. It is demonstrated by replacement with alanine one by one that $Lys^{16}$, $Leu^{17}$ and $Phe^{20}$ play a critical role in this process. This shows that the $A\beta^{16-20}$ residues constitute the section by which two adjacent Aβ peptides bind to each other in the aggregation of Aβ peptides. It has been shown that the conformation of Aβ significantly affects its aggregation capabilities: when the major secondary structure is α-helix, the aggregation is slower; whereas the major secondary structure is β-sheet, the aggregation is more quickly.

Under certain conditions, the exposure of β-sheet-rich hydrophobic regions will lead to the aggregation of Aβ and the formation of oligomers, and eventually the formation of insoluble material deposited in the intercellular space of neurons. This may results in neurotoxicity and the increased activities of glial cells in brain, producing inflammatory mediators and complement which may together form amyloid plaques.

The increased hydrophobic charge of a molecule is one of the major causes of the Aβ aggregation. As compared with $A\beta^{1-40}$, $A\beta^{1-42}$ has two more residues, which not only increase the hydrophobicity of Aβ, making it easier to aggregate, but also improve the stability of aggregates, allowing them to selectively deposit in amyloid plaques in early stage. $A\beta^{1-42}$ may be the initial factor of the process which forms oligomers, fiber and the plaque from soluble Aβ. (Younkin, S. G. 1995. Evidence that A beta 42 is the real culprit in Alzheimer's disease. Ann. Neurol. 37: 287-288; Matsuok Y, Saito M, Lafrancois T, et al. Noval therapeutic approach for the treatment of Alzheimer's disease by peripheral administration of agents with an affinity to β-amyloid[J]. J Neurosci, 2003, 23(1): 1-5).

Jarrett et al. speculated that Aβ1-42 served as a "seed" to initiate the deposition of Aβ. Other monomer then gradually gathered around the nucleus and extended the peptide chain to form fibrils (elongation), and the fibrils further spread and finally formed plaques. (Jarrett J T, Lansbury P T Jr. Seeding "one-dimensional crystallization" of amyloid: a pathogenic mechanism in Alzheimer's disease and scrapie? Cell. 1993, (6): 1055-1058).

It is believed that the aggregation and deposition of Aβ and the formation of senile plaque and the accompanying neuron damage constitute the central parts of the pathological mechanisms of AD. Therefore, inhibiting the aggregation of Aβ peptide and promoting the degradation and clearance of Aβ peptide may be the fundamental means of preventing and/or treating AD.

Recent studies on development of drugs for Aβ focus on the aspect of reducing the formation of Aβ, increasing the Aβ clearance, preventing or reversing Aβ aggregation, and inhibiting the toxicity of Aβ, and the like. Researchers in Medicine School of Washington University found that AD mice could surprisingly restore their brain cell functions after clearance of amyloid plaques in their brain, which indicates a promising prospect of drugs targeting Aβ. Among a variety of drugs against Aβ, β-sheet blockers draw increasing attention of the researchers.

There are two main types of drugs belonging to β-sheet blockers:

(1) Based on the realization that the low molecular weight amino-glycoprotein (gly-cosaminoglycan, GAGs) could stabilize the β-amyloid plaques and inhibit the degradation of the plaque, Neurochem Inc. in Canada designed and synthesized GAG derivatives. In vivo experiments showed that such low molecular weight GAG analogues can significantly reduce levels of β-amyloid in plasma and brain and inhibit Aβ aggregation, and thus can be used for the treatment of AD. One such low molecular weight GAG analogue, designated as Alzhemed, has been in clinical trials phase III.

(2) Chacón et al. induced behavior disorder in rats by intraperitoneal injection of fibrotic Aβ, and then assessed β-sheet breaker peptide consisting of five amino acid residues (five-amino-acid beta-sheet breaker peptide, iAbeta5p) for their protection effects on neuron. Results showed that iAbeta5p could not only inhibit the formation of Aβ fibrils, but also degrade Aβ fibrils (Chacón M A, Barrïa M I, Soto C, et al., Beta-sheet breaker peptide prevents beta-induced spatial memory impairments with partial reduction of amyloid deposits. Mol. Psychiatry. 2004, 9(10): 953-61). The drug of iAbeta5p has been in clinical trials phase III.

In the art, there remains need of new active drugs which can specifically bind to monomer of β-amyloid ($A\beta_{1-42}$), stabilize its normal spatial structure, inhibit its formation of β-sheet, and prevent the formation of soluble β-amyloid oligomers and β-amyloid plaque. Said drug should be able to inhibit the aggregation of Aβ peptide, promote the degradation and clearance of Aβ peptide, and thus can be used for prevention and/or treatment of AD.

SUMMARY OF THE INVENTION

One object of the invention is to provide a polypeptide which can specifically bind to monomer of β-amyloid ($A\beta_{1-42}$), stabilize its normal spatial structure, inhibit its formation of β-sheet, and prevent the formation of soluble β-amyloid oligomers and β-amyloid plaque. Furthermore, the polypeptide could degrade Aβ fibrils. The polypeptide can be named as β-sheet breaker peptide.

Surprisingly, the inventor found that polypeptides comprising the following amino acid sequence could achieve the above-mentioned object (SEQ ID NO:5):

```
His-X1-X2-Leu-X3-Phe-Phe-X4-Glu-Asp
``` wherein:
X1 can be a lysine residue (Lys,K) or a glutamine residue (Gln,Q);
X2 can be a lysine residue (Lys, K) or a glutamine residue (Gln,Q);
X3 can be a valine residue (Val,V) or a proline residue (Pro,P);
X4 can be a alanine residue (Ala,A) or a glutamate residue (Glu,G).

Therefore, in the first aspect of the invention, provided are polypeptides comprising the above-described amino acid sequence.

Since the above polypeptides can specifically bind to monomer of β-amyloid ($A\beta_{1-42}$), stabilize its normal spatial structure, inhibit its formation of β-sheet, prevent the formation of soluble β-amyloid oligomers and β-amyloid plaque, and degrade Aβ fibrils, they can be used for prevention and/or treatment of AD.

Thus, in the second aspect of the invention, provided is use of the polypeptides of the invention in the manufacture of a medicament for prevention and/or treatment of AD.

In the third aspect of the invention, provided are pharmaceutical compositions comprising one or more polypeptides of the invention and a pharmaceutically acceptable carrier.

In the fourth aspect of the invention, provided is a method for prevention and/or treatment of AD in a subject, comprising administration of an effective amount of the polypeptides of the invention to the subject.

DESCRIPTION OF THE ACCOMPANYING FIGURES

FIG. 1 shows the steps of an exemplary method for preparing the polypeptides of the invention and the test results of the prepared products.

FIG. 5 shows the electron microscopy results of fibril formation of $A\beta_{1-42}$ peptide after the incubation of $A\beta_{1-42}$ peptide of 11.07 μmol/L with different peptides of 44.30 μmol/L at 37° C. for 5 days.

FIG. 7 shows the results of immunohistochemical staining on slices of neurons in hippocampal CA1 region of mice from various groups, using anti-APP N-terminal antibody and anti-Aβ antibody, magnification=400×.

FIG. 8 shows the Congo Red staining results of temporal cortex and hippocampus of mice from various groups, magnification=400×.

DETAILED DESCRIPTION OF THE INVENTION

Disclosed herein are amino acid sequences of a series of polypeptides. It can be appreciated by the person skilled in the art that the sequence in which an amino acid residue is shown in single-letter or three-letter form indicates the amino acid sequence of a polypeptide from its N-terminal (amino-terminal) to its C-terminal (carboxy-terminal). For example, when a polypeptide is indicated as (SEQ ID NO: 3) "His-Gln-Lys-Leu-Val-Phe-Phe-Ala-Glu-Asp" or "HQKLVFFAED", it means that the sequence of this polypeptide is "N-terminal-His-Gln-Lys-Leu-Val-Phe-Phe-Ala-Glu-Asp-C-terminal", i.e., "N-terminal-HQKLVFFAED-C-terminal".

In the first aspect of the invention, provided are polypeptides comprising the following amino acid sequence (SEQ ID NO:5):

```
His-X1-X2-Leu-X3-Phe-Phe-X4-Glu-Asp
``` wherein:
X1 can be a lysine residue (Lys,K) or a glutamine residue (Gln,Q);
X2 can be a lysine residue (Lys, K) or a glutamine residue (Gln,Q);
X3 can be a valine residue (Val,V) or a proline residue (Pro,P);
X4 can be a alanine residue (Ala,A) or a glutamate residue (Glu,G).

The polypeptides of the invention could comprise, substantially consist of, or consist of the above-mentioned amino acid sequence.

In one embodiment of the invention, provided is a polypeptide having the following sequence, which is designated as H101 in the invention:

```
H101:
                                           (SEQ ID NO: 1)
His-Lys-Gln-Leu-Val-Phe-Phe-Glu-Glu-Asp
(HKQLVFFEED).
```

In another embodiment of the invention, provided is a polypeptide having the following sequence, which is designated as H102 in the invention:

```
H102:
                                           (SEQ ID NO: 2)
His-Lys-Gln-Leu-Pro-Phe-Phe-Glu-Glu-Asp
(HKQLPFFEED).
```

In another embodiment of the invention, provided is a polypeptide having the following sequence, which is designated as H103 in the invention:

```
H103:
                                           (SEQ ID NO: 3)
His-Gln-Lys-Leu-Val-Phe-Phe-Ala-Glu-Asp
(HQKLVFFAED).
```

Disclosed are amino acid sequences of a series of polypeptides. It is apparent that various modifications can be made to a polypeptide of the invention. Said modifications include but are not limited to: the hydroxylation of proline and lysine; phosphorylation of the hydroxyl groups on serine or threonine residues; methylation of o-amino group on side chain of lysine, arginine and histidine; acetylation of N-terminal amino and, in some cases, amidation of C-terminal carboxyl. It should be understood that, it is apparent for the person skilled in the art to make these modifications based on the amino acid sequences of the polypeptides of the invention, and these modified polypeptides comprising the disclosed amino acid sequences are also encompassed within the scope of the present invention.

These polypeptides of the invention can serve as β-sheet breaker peptides. Since the polypeptides of the invention can specifically bind to monomer of β-amyloid ($A\beta_{1-42}$), stabilize its normal spatial structure, inhibit its formation of β-sheet, and prevent the formation of soluble β-amyloid oligomers and β-amyloid plaque, and degrade Aβ fibrils, they can be used as medicaments for prevention and/or treatment of AD.

Thus, in another aspect of the invention, provided are use of the polypeptides of the invention in the manufacture of a medicament for prevention and/or treatment of AD.

The term "prevent", "preventing" or "prevention" as used herein refers to reducing the risk of the subject being suffered by the disease, or delaying the time point of the onset of diseases or associated symptoms. The term "treat", "treating" or "treatment" as used herein may not necessarily refer to completely cured, but may refer to ameliorating the symptoms of underlying diseases and/or reducing one or more types of underlying cellular, physiological or biochemical causes or mechanisms which could induce the symptoms. It should be appreciated that "ameliorating" as used herein is relative to the ill conditions and refers to not only the physiological conditions, but also the molecular patterns, of the disease.

Also provided are pharmaceutical compositions comprising one or more polypeptides of the invention and a pharmaceutically acceptable carrier.

The term "pharmaceutically acceptable carrier" as used herein refers to a substance which will not cause any undesirable effects in term of biology or other aspects. That is to say, the substance can be administered to a subject together with the polypeptides of the invention and will not cause any biologically undesirable effects, and will not interact with any other component in the pharmaceutical compositions in an undesirable manner. It is evident and well known to the person skilled in the art that the carrier should be chosen to minimize any degradation of the active ingredients and any adverse side effects in the subject.

Generally, the pharmaceutical compositions of the invention comprise at least one of polypeptides of the invention and one or more pharmaceutically acceptable carriers. Suitable carriers include, but are not limited to: anti-oxidants, preservatives, coloring agents, flavoring agents and diluents, emulsifiers, suspending agents, solvents, fillers, bulking agents, buffering agents, vehicles, extenders, excipients and/or pharmaceutical adjuvants. For example, a suitable carrier can be normal saline solution, citrate buffer or artificial CSF, and other substances which may be added into a conventional parenteral composition. Neutral buffered saline or saline mixed with serum albumin are examples of the carriers. The person skilled in the art can easily determine various buffering agents which can be used in the compositions and dosage forms of the invention. Typical buffering agents include, but are not limited to, pharmaceutically acceptable weak acids, weak bases or combinations thereof. Preferably, the buffering components are water-soluble substances, such as phosphoric acid, tartaric acid, lactic acid, succinic acid, citric acid, acetic acid, ascorbic acid, aspartic acid, and glutamic acid, and the salts thereof.

The primary solvent in the carriers can be aqueous or non-aqueous in nature. Furthermore, the carriers can include other pharmaceutical acceptable excipients which can be used to improve or maintain the pH, permeability, viscosity, clarity, color and asepsis, stability, dissolution rate, or odor of the formulation. Pharmaceutical compositions of the invention can further include other pharmaceutical acceptable carriers which can be used to improve or maintain the release rate of the polypeptides of the invention. Such carriers are known to the person skilled at preparing a sustained release formulation.

When the pharmaceutical compositions of the invention have been formulated, they can be stored in sterile tubes in the forms of solution, suspension, gel, emulsion, solid or dehydrated or lyophilized powder. These formulations can also be stored in ready-to-use form, in lyophilized powder form that is to be reconstituted before use, or in solution form that is to be diluted before use. Preferably, the pharmaceutical compositions of the invention are provided in the form of sterile tubes of a single dose, and stored at 2-8° C. before use. Before administration, the pharmaceutical compositions of the invention can be diluted by any suitable sterile buffer, such as citrate buffer, as described above.

Also provided is a method for prevention and/or treatment of AD in a subject, comprising administration of an effective amount of the polypeptide of the invention to the subject.

The term "effective amount" as used herein refers to the amount of the compound used that is effective to prevent the onset of the diseases or associated symptoms, or to ameliorate one or more etiologies or symptoms of the disease or condition. The ameliorating may be alleviating or improving but not necessarily eliminating. For the polypeptides of the invention, its prevention and/or treatment effective amount should be varied depending on the individual and the polypeptide used. The prevention and/or treatment effective amount of polypeptides used should also be varied depending on many factors, such as age, shape, weight, conditions of the individual. For a particular subject, determination of the prevention and/or treatment effective amount of polypeptides of the invention is within the knowledge of the person skilled in the art.

When the polypeptides or the preventing/treating methods of the invention are applied to AD subjects, significant effects can be observed, such as the inhibition of Aβ accumulation in brain tissue of subjects, the reduction of the number and the area of amyloid plaques, and the improvement of AD symptoms. For example, they can be used to improve activity and attention and reduce response time, to improve pronunciation, facial expression, posture, smell, sexuality, sexual function and emotional status, and to induce a happy emotion. In another embodiment of the present invention, the polypeptides of the invention can be appropriately administered to AD patients as a cognitive enhancing agent, thereby increasing learning abilities, particularly those damaged by dementia, or inhibiting the cognitive decline and/or dementia.

Preparation of the Polypeptides of the Invention

The polypeptides of the invention can be prepared through any methods for preparing polypeptides that are known to persons skilled in the art.

The polypeptides of the invention can be synthesized through chemical synthesis. The synthesis of a polypeptide can be carried out in solution. Alternatively, solid-phase synthesis can also be used. Solid-phase synthesis methods of polypeptide include Fmoc solid-phase synthesis and tBoc solid-phase synthesis. Generally, the synthesis methods of polypeptide are carried out from the C-terminal (carboxyl-terminal) to the N-terminal (amino-terminal) of the polypeptide.

In one embodiment of the invention, the polypeptides of the invention are synthesized through Fmoc solid-phase synthesis and purified through HPLC. FIG. 1 exemplarily shows the main steps of this embodiment for preparing and purifying a polypeptide of the invention, H101, and the test results of the prepared polypeptide. In this embodiment, the polypeptide is synthesized on synthesis column by using a solid-phase polypeptide synthesizer, such that the difficulty of product purification can be significantly reduced. In order to minimize side reactions, synthesis column and the side chains of the added amino acids are protected. The C-terminal is free and must be activated before the reaction. After the polypeptides of the invention have been synthesized through Fmoc solid-phase synthesis and purified through preparative high performance liquid chromatography (HPLC) column, they can be identified by mass spectrometry (MS) analysis. It should be appreciated that all the polypeptides of this invention can be prepared, purified and identified in a manner similar to the embodiment as described above.

The polypeptides of the invention can also be produced through recombinant genetic engineering. In short, a polynucleotide encoding polypeptides of the invention can be synthesized and then transformed into a suitable host cell using the known method in the art. Then the transformed polynucleotide can be expressed, and the expressed product can be purified or processed to obtain the polypeptides of the invention.

EXAMPLES

The invention is further illustrated by the following examples, with which the ordinary person skilled in the art may obtain better understanding of the invention. These examples are only provided to exemplarily illustrate the invention and are not intended to be interpreted as any limitation. Efforts have been made to ensure the accuracy of related numbers (such as number, temperature). However, it should be appreciated that some errors and deviations may exist. Unless otherwise indicated, the parts are parts by weight, the temperature is the ambient temperature or expressed in ☐, the pressure is equal or near to atmospheric pressure.

Example 1

Preparation of the Polypeptides of the Invention

In this example, a polypeptide of the invention, H101, was first synthesized through Fmoc/tBu solid-phase synthesis. The sequence of H101 is shown as follows:

```
                                        (SEQ ID NO: 1)
    His-Lys-Gln-Leu-Val-Phe-Phe-Glu-Glu-Asp.
```

In the synthesis method used in this example, the following substances were used as starting materials: Fmoc-Asp (OtBu)-Wang Resin (0.37 mmol/g), Fmoc-Val-OH, Fmoc-Glu(OtBu)-OH, Fmoc-His(trt)-OH, Fmoc-Gln(trt)-OH, Fmoc-Leu-OH, Fmoc-Lys(Boc)-OH, and Fmoc-Phe-OH.

Figure 1A:
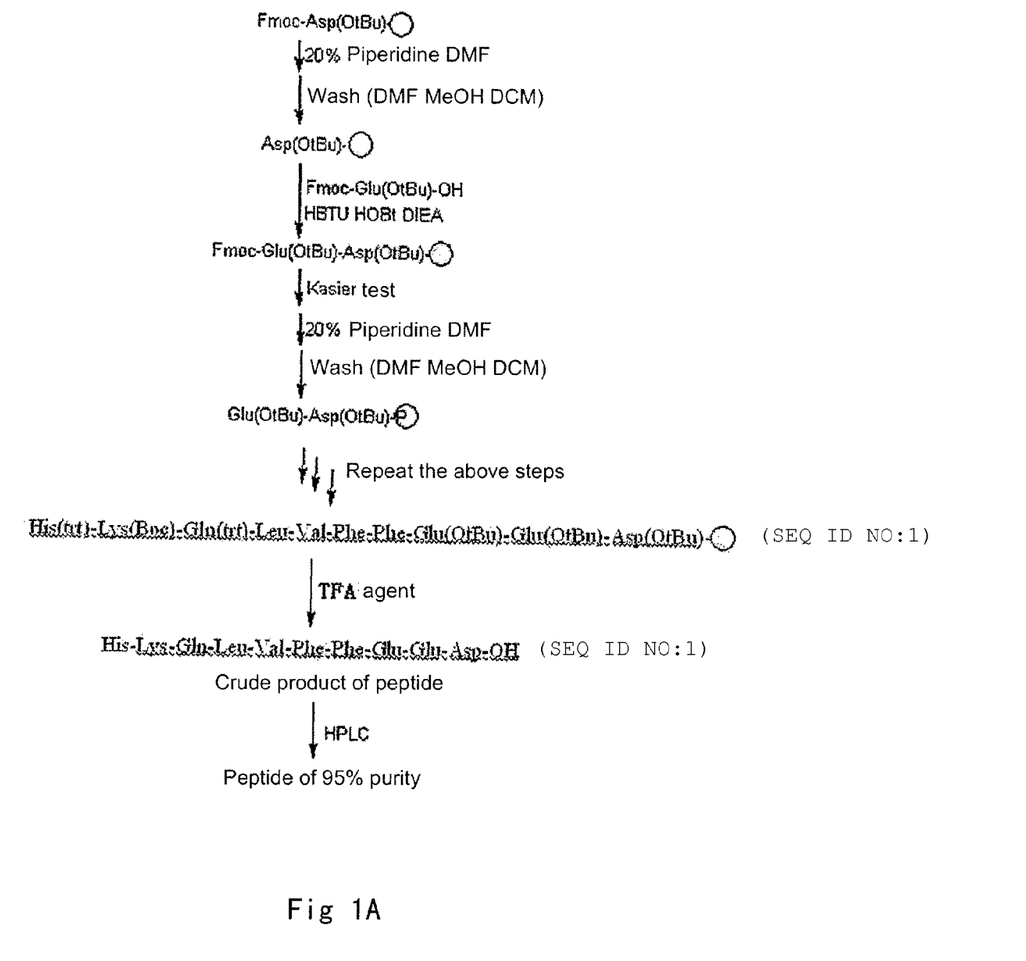
FIG. 1A shows the main steps of an exemplary method for synthesizing and purifying a polypeptide of the invention, H101.

The main steps of synthesis and purification methods used in this example are shown in FIG. 1A.

The formulation of TFA agent used in the embodiment as shown in FIG. 1A is: [TFA:$H_2O$:ethylene mercaptan:phenol=92.5:2.5:2.5:2.5, (v/v), mixed].

Figure 1B:
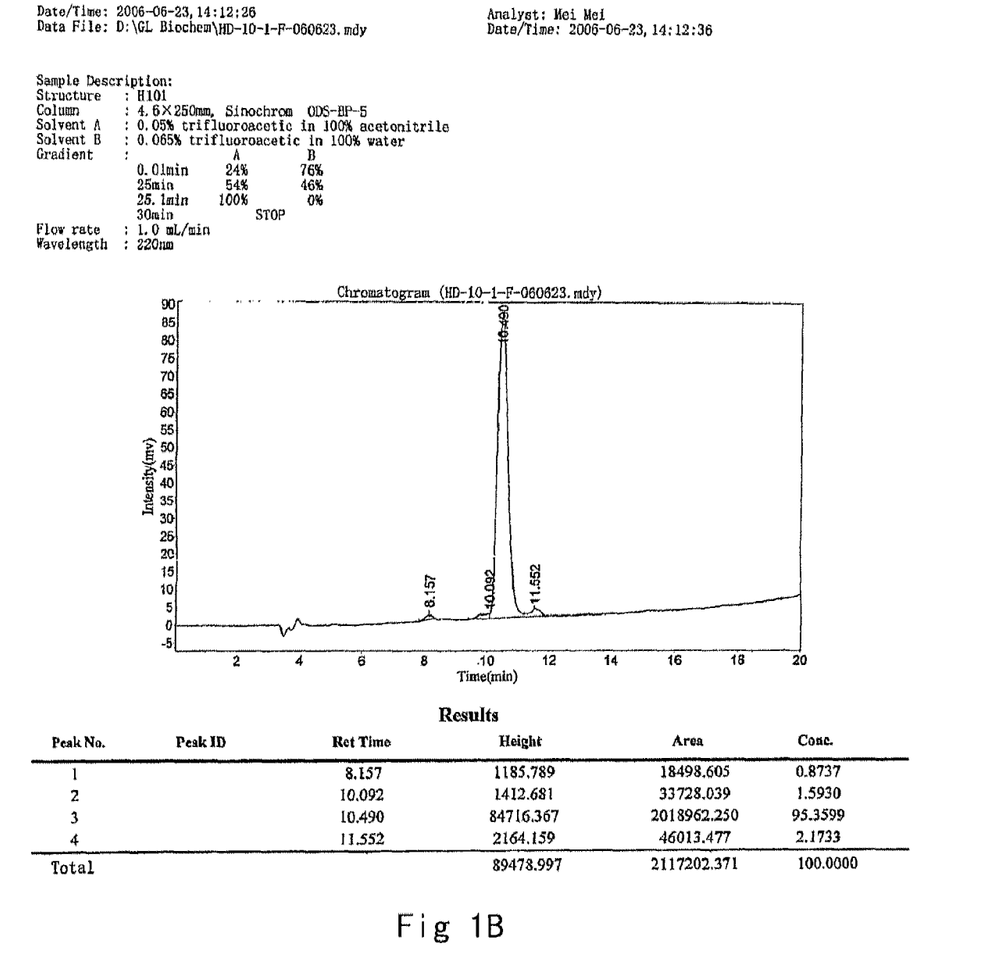
FIG. 1B shows the chromatography result of H101.

The crude product of the prepared peptide was purified through HPLC, producing the final product with the purity >95%. The results of HPLC are shown in FIG. 1B.

Figure 1C:
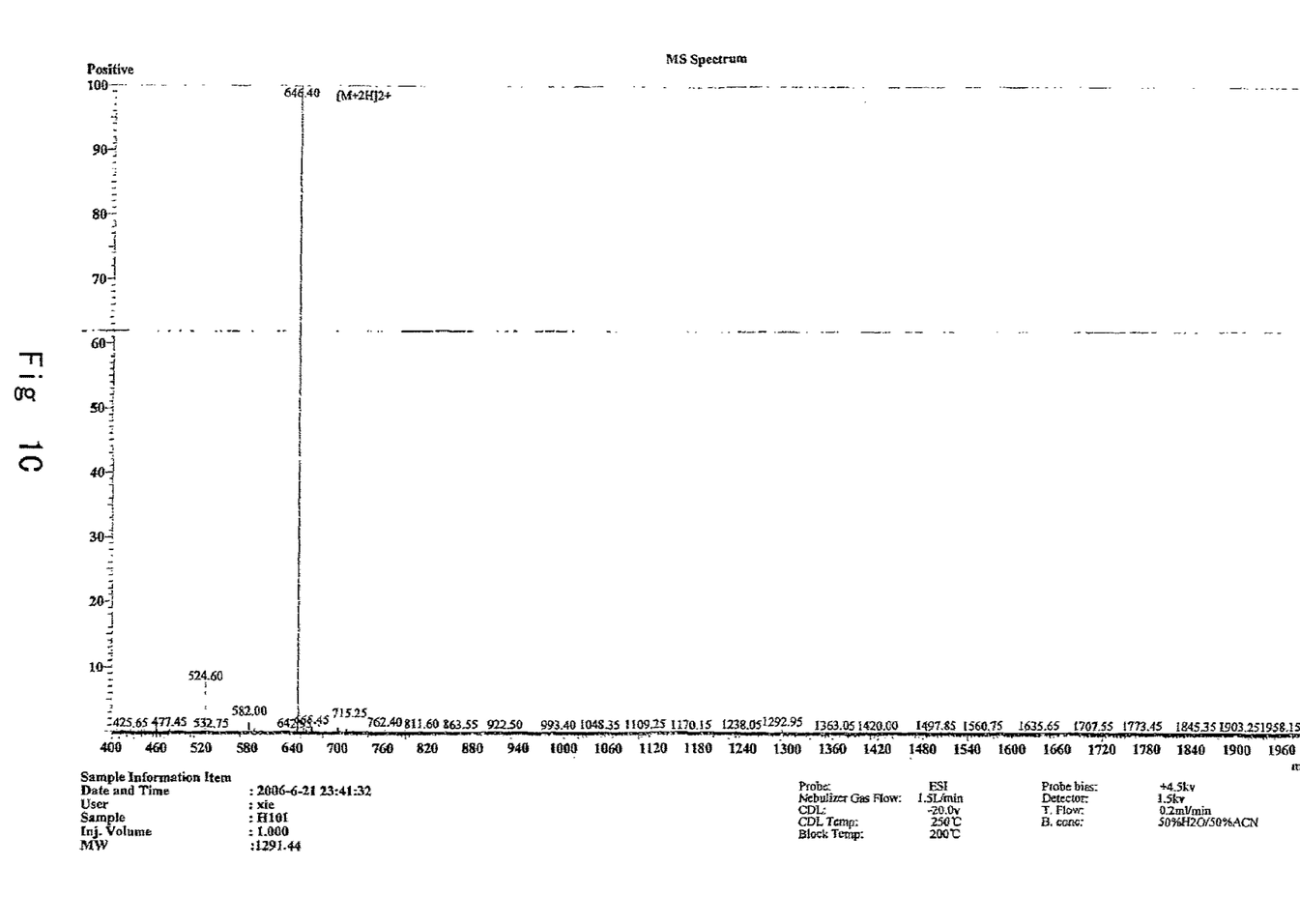
FIG. 1C shows the mass spectrum result of H101.

Polypeptide H101 prepared and purified as above were identified by mass spectrometry (MS) analysis and sequenced. The results of mass spectrometry analysis are shown in FIG. 1C. The results of identification and sequencing showed that the polypeptide prepared by the above method had the expected sequence and molecular weight.

Then, the following polypeptides of the invention were prepared in a manner similar to the method as described above:

```
    H102:
                                        (SEQ ID NO: 2)
    His-Lys-Gln-Leu-Pro-Phe-Phe-Glu-Glu-Asp;

H103:
                                        (SEQ ID NO: 3)
    His-Gln-Lys-Leu-Val-Phe-Phe-Ala-Glu-Asp.
```

The results of sequencing and identification of these polypeptides demonstrate that the synthesis and purification method as described in this Example is suitable for a variety of polypeptides of the invention. The polypeptides prepared by the described method have the expected sequences and molecular weights. Further, the purity of the polypeptide products obtained by the purification method as described above can be more than 95%.

Example 2

The Effects of the Polypeptides of the Invention on β-Amyloid Proteins

Materials and Methods

1. Reagents: $A\beta_{1-42}$ (purity >98%), Vitamin E, Thioflavin T (ThT), Thiazolyl Blue (MTT), dimethyl sulfoxide (DMSO), all from Sigma-Aldrich, Inc.; MEM medium, fetal bovine serum (FBS), and trypsin, all from Gibco-BRL Inc. The polypeptides of the invention, H101, H102, and H103, were prepared as described in Example 1. Furthermore, a pentapeptide, Leu-Pro-Phe-Phe-Asp, was prepared in a manner similar to those described in Example 1. This pentapeptide has the same sequence as the β-sheet breaker peptide, iAbeta5, invented by Soto-Jara et al., and designated as L5 herein. The pentapeptide L5 was used as a control in this and the following Examples. These polypeptides were all synthesized by GL Biochem (Shanghai) Ltd., purified through High Performance Liquid Chromatography (HPLC), and identified through mass spectrum (MS) analysis with a purity >95%.

2. Thioflavin T (ThT) fluorescence analysis and electron microscopy: Thioflavin T (ThT) fluorescence analysis was used to analyze the Aβ aggregation, since ThT fluorescence intensity could reflect the degree of Aβ aggregation, It was reported that Vitamin E (VE) could effectively inhibit Aβ aggregation and the fibril formation, and thus Vitamin E was used in this study as a positive control. $A\beta_{1-42}$ lyophilized powder was formulated in 50 mmol/L PBS (pH7.4) to obtain a solution in the concentration of 22.15 μmol/L; the above four polypeptides (H101, H102, H103 and L5) were also formulated in 50 mmol/L PBS (pH7.4) to obtain the solutions in the concentration of 88.61 μmol/L; and Vitamin E was formulated in PBS containing 0.2% Tween-80 to obtain an emulsion in the concentration of 88.61 μmol/L. In the experiment, the solution of $A\beta_{1-42}$ peptide was mixed in equal-volume with the solution of each of the polypeptides, such that their final concentrations were 11.07 μmol/L and 44.30 μmol/L, respectively. The solution of $A\beta_{1-42}$ peptide was mixed in equal-volume with Vitamin E emulsion and used as a positive control; and the solution containing $A\beta_{1-42}$ alone was used as a negative control. Each solution was incubated at 37° C. for 24 h, and 10 μl was taken out from each group and added into 990 μl of 3.0 μmol/L ThT phosphate buffer. ThT fluorescence intensity was measured at the excitation wavelength of 453 nm and emission wavelength of 478~486 nm.

3. The dose-effect and time-effect relationships of the polypeptides of the invention on $A\beta_{1-42}$: polypeptide H102 was formulated in PBS (as described above) to obtain a series of concentrations, and $A\beta_{1-42}$ was added into the solutions to the concentration of 11.07 μmol/L. The resulted solutions were incubated at 37° C. for 24 hours, and samples were taken and measured for ThT fluorescence intensity, in order to determine the dose-effect relationship of the polypeptides of the invention on $A\beta_{1-42}$. Solutions containing H102 of 44.30 μmol/L and Aβ1-42 of 11.07 μmol/L, or Vitamin E of 44.30 μmol/L and $A\beta_{1-42}$ of 11.07 μmol/L, respectively, were incubated at 37° C. Samples were taken and measured for ThT fluorescence intensity at the time points of 12 hours (12 h), 1 day (1 d), 3 days (3 d), 5 days (5 d) and 7 days (7 d) after the incubation, in order to determine the time-effect relationships of various polypeptides on $A\beta_{1-42}$. In the meantime, a solution containing $A\beta_{1-42}$ peptide alone was incubated and used as a negative control.

4. Electron microscopy: to further investigate the fibril formation, solutions containing various polypeptides of 44.30 μmol/L, and $A\beta_{1-42}$ of 11.07 μmol/L, respectively, were incubated at 37° C. for 5 days. Samples of 5 μl were taken from each group, dropped onto a 300-mesh deionized copper mesh with carbon support film, and left to stand at room temperature for 15 min. The samples were negatively stained in dark by 2% uranyl acetate for 2 min. After drying, the samples were observed under a transmission electron microscope. In the meantime, a solution containing $A\beta_{1-42}$ peptide alone was incubated for 5 days and used as a negative control.

5. Cytotoxicity test: a commonly-used cell line, human neuroblastoma SH-SY5Y, was used in the assay of cytotoxicity, which was purchased from Xuanwu Hospital of Capital Medical University and cultured in MEM medium (supplemented with 10% (v/v) fetal bovine serum) by conventional methods, in a 37° C., 5% $CO_2$ incubator. The cell line was subcultured once every 5 days. When the SH-SY5Y cells grew stably in the logarithmic phase, the cells were inoculated into a 96 well plates (Costar) in a density of $1.0\times10^4$/ml, with 200 μl of medium added per well. After 24 hours, the medium was replaced by serum-free medium, and $A\beta_{1-42}$ was added to the concentration of 5 μmol/L. The wells were divided into several groups. The above four polypeptides (H101, H102, H103 and L5) were added into the medium of each group to the concentrations of 10 μmol/L, 20 μmol/L and 40 μmol/L, respectively. The group of cells into which the serum-free medium alone was added without addition of $A\beta_{1-42}$ and polypeptides was used as a positive control, and the group of cells into which $A\beta_{1-42}$ peptide was added without addition of the above polypeptides was used as a negative control. At 72 hours after the addition of the polypeptides, 20 μl of 3-(4,5-dimethyl-2-thiazolyl)-2,5-diphenyltetrazole bromide (MTT) (5 mg/ml) was added into each well, and the plate was incubated at 37° C. for 4 hours. Then the original culture medium was discarded, and 200 μl of DMSO was added into each well. The plate was left to stand for 10 min and then shaken for 1 min, allowing the Formazane particles to be completely dissolved. Then the optical density (OD) at 492 nm was measured on an automatic microplate reader.

6. Statistical analysis: the t test method was used for data comparison between the two groups, and F test method was used for data comparison among more than two groups.

Results

1. The inhibition effects of various tested polypeptides on the $A\beta_{1-42}$ aggregation and fibril formation.

ThT fluorescence analysis was used to assess the effects of various polypeptides and VE on $A\beta_{1-42}$ aggregation and fibril formation. $A\beta_{1-42}$ alone in PBS solution could produce an extremely high fluorescence intensity, indicating that Aβ1-42 can self-aggregate and form Aβ fibrils. The fluorescence intensity resulted from the negative control solution, which contains $A\beta_{1-42}$ alone and do not contain any test polypeptide or Vitamin E, was normalized to 100%. The inhibition rates of various tested polypeptides on the $A\beta_{1-42}$ aggregation and fibril formation were calculated (%). Results are shown in Table 1. (Note: The data shown in Table 1 had been subtracted by the background fluorescence produced by the equipment system itself).

TABLE 1 the inhibition effects of various polypeptides on Aβ aggregation (%)

| | Polypeptide tested | | | | |
|---|---|---|---|---|---|
| | L5 | H101 | H102 | H103 | Vitamin E |
| Inhibition (%) | 25.74 | 24.79 | 27.84 | 14.91 | 24.85 |

As shown in the above Table 1, H102 exhibits the highest inhibition effect on Aβ1-42 aggregation, followed by L5, Vitamin E, H101 and H103, respectively.

Figure 2:
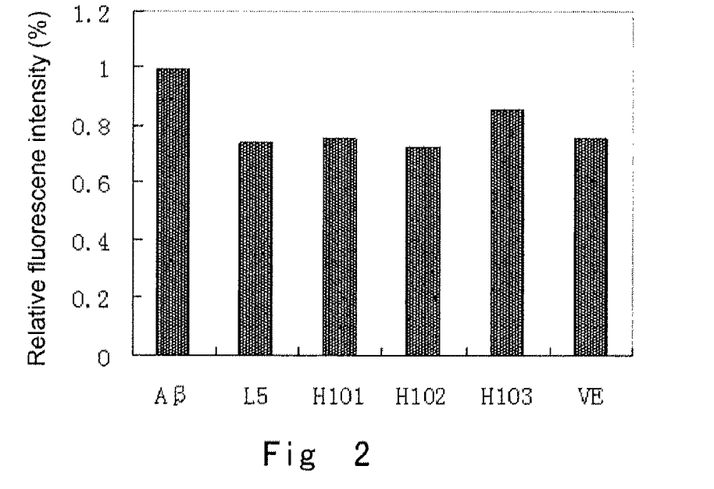
FIG. 2 shows results of Thioflavin T fluorescence analysis of aggregation of $A\beta_{1-42}$ peptide and formation of the fibrils, demonstrating the effects of the polypeptides of the invention on the fluorescence intensity resulted from the Aβ aggregation. A given concentration of $A\beta_{1-42}$ peptide and polypeptides of the invention, H101, H102 or H103, or vitamin E (VE) or L5, were incubated at 37° C. for 24 hours, and then ThT fluorescence intensities were measured. n=5; * denotes P<0.05 as compared with the group of $A\beta_{1-42}$.

The results shown in the above Table were plotted as a histogram shown in FIG. 2.

As shown in FIG. 2, H102 can remarkably inhibit the $A\beta_{1-42}$ aggregation and fibril formation; Vitamin E, when incubated with $A\beta_{1-42}$, can also remarkably inhibit the $A\beta_{1-42}$ aggregation and fibril formation. However, the effects of VE are weaker than those of H102.

Figure 3:
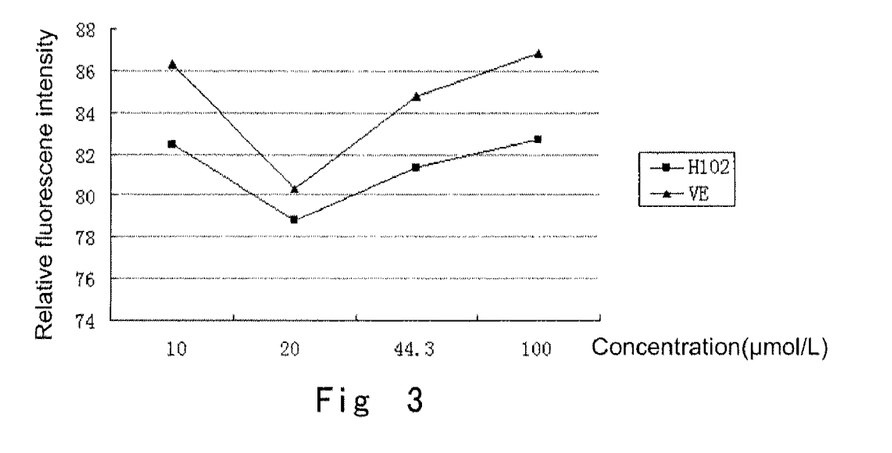
FIG. 3 shows the dose-dependent curve of inhibition of the fibril formation of $A\beta_{1-42}$ by H102 and vitamin E. $A\beta_{1-42}$ peptide of 11.07 μmol/L and H102 or vitamin E at the concentrations of 10 μmol/L, 20 μmol/L, 44.30 μmol/L, and 100 μmol/L, respectively, were incubated at 37° C. for 24 hours, and then ThT fluorescence intensities were measured. n=5.

2. The dose-effect relationships of the polypeptides of the invention on $A\beta_{1-42}$: FIG. 3 shows the results of ThT fluorescence analysis which were obtained from the incubation (37° C. for 24 h) of H102 or Vitamin E at various concentrations with $A\beta_{1-42}$ peptide of 11.07 μmol/L. As shown in FIG. 3, the effects of H102 and Vitamin E on Aβ fibril formation are dose-dependent, and the inhibition rate of H102 is higher than that of Vitamin E at every point of concentration. Furthermore, the most effective concentration of H102 and Vitamin E is about 20 μmol/L.

Figure 4:
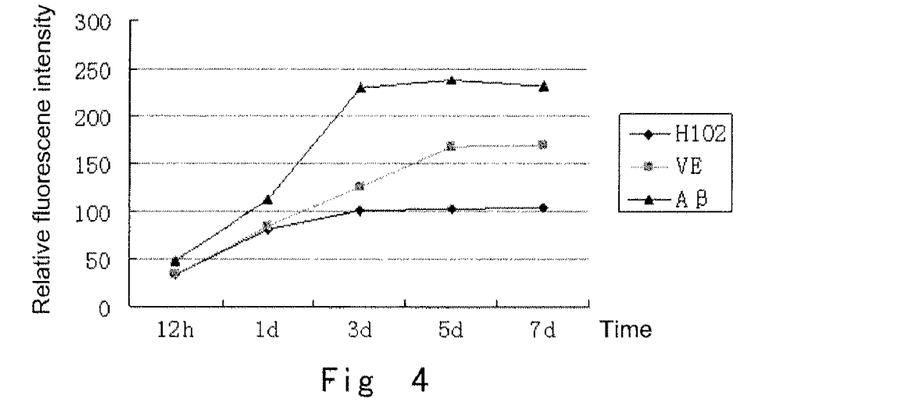
FIG. 4 shows the time-dependent curve of inhibition of the fibril formation of $A\beta_{1-42}$ by H102 and vitamin E. $A\beta_{1-42}$ peptide of 11.07 μmol/L and H102 or vitamin E at the concentration of 44.30 μmol/L, were incubated at 37° C., and then ThT fluorescence intensities were measured at time points of 12 hrs, 1 day, 3 days, 5 days, and 7 days. n=5.
Figure 5A:
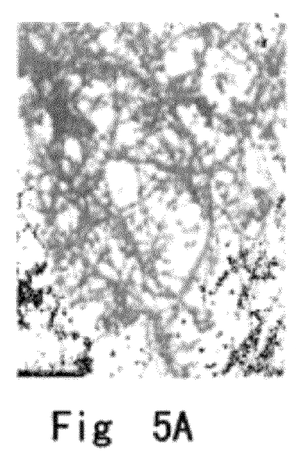
FIG. 5A: the electron microscopy results obtained by incubation of $A\beta_{1-42}$ alone for 5 days, magnification=35,000×.
Figure 5B:
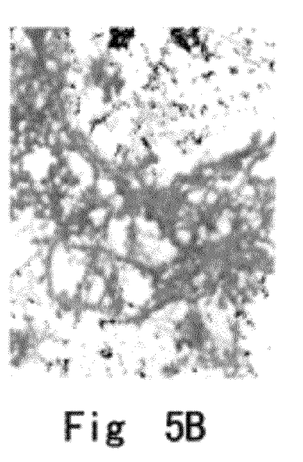
FIG. 5B: the electron microscopy results obtained by incubation of $A\beta_{1-42}$ alone for 5 days, magnification=50,000×.
Figure 5C:
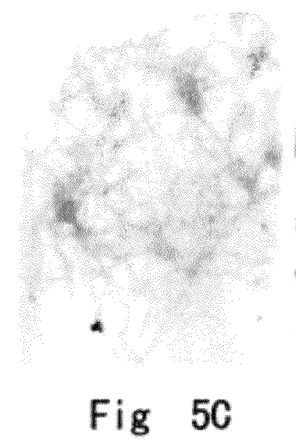
FIG. 5C: the electron microscopy results obtained by incubation of $A\beta_{1-42}$ with L5 peptide for 5 days, magnification=35,000×.
Figure 5D:
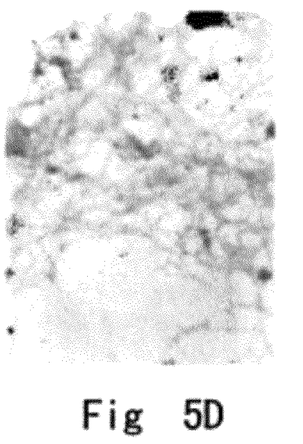
FIG. 5D: the electron microscopy results obtained by incubation of $A\beta_{1-42}$ with H101 peptide for 5 days, magnification=35,000×.
Figure 5E:
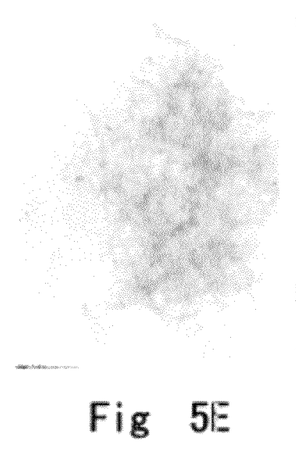
FIG. 5E: the electron microscopy results obtained by incubation of $A\beta_{1-42}$ with H102 peptide for 5 days, magnification=35,000×.
Figure 5F:
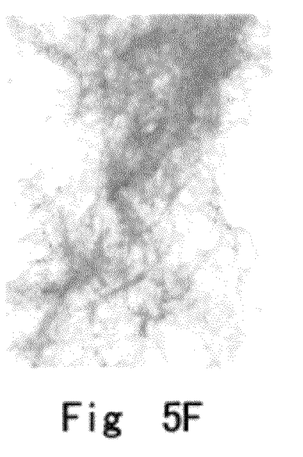
FIG. 5F: the electron microscopy results obtained by incubation of $A\beta_{1-42}$ with H103 peptide for 5 days, magnification= 35,000×.

3. The time-effect relationships of the polypeptides of the invention on $A\beta_{1-42}$: FIG. 4 shows the results of ThT fluorescence analysis which were obtained from the incubation of H102 or Vitamin E with $A\beta_{1-42}$ peptide of 11.07 μmol/L for various periods. As shown in FIG. 4, when $A\beta_{1-42}$ peptide of 11.07 μmol/L was incubated alone, the resulted fluorescence intensity is low in the first 24 h and rapidly increases on the third day and then increases in a platform manner. The fluorescence intensities resulted from the groups of H102 and VE are significantly weaker at each time point, and the most effective results are observed in the H102-treated group. Change of curve can be characterized by the time point $T_{1/2}$ at which the fluorescence intensity reaches the half-peak, the $T_{1/2}$ of the group of Aβ alone occurs on the third day, and the $T_{1/2}$ of the group of H102 and Vitamin E are delayed to the fourth day.

4. Results of electron microscopy:

FIG. 5 shows the results of electron microscopy about $Aβ_{1-42}$ peptide fibril formation, which were obtained by incubation of various polypeptides of 44.30 μmol/L with $Aβ_{1-42}$ peptide of 11.07 μmol/L at 37° C. for 5 days, respectively. As shown in the figures, when Aβ was incubated alone for 5 days, a large number of Aβ fibrils are formed, with a diameter of about 8 to 10 nm and a length of about 0.5 to 5 μm. The fibrils are aggregated in a prick-type crystallization, with branches and even woven into networks, interspersed with a small amount of amorphous structures in an aggregation state (FIGS. 5A and 5B, the control group). While Aβ was incubated with L5 for 5 days, the formed Aβ fibrils are much thinner, with a diameter of about 4 to 8 nm and a length of 0.3 to 5 μm. The fibrils are woven into networks, interspersed with a very small amount of amorphous structures in an aggregation state (FIG. 5C). While Aβ was incubated with H101 for 5 days, the formed Aβ fibrils have a diameter of about 5 to 8 nm and a length of 0.5 to 5 μm. The fibrils are woven into networks with branches, interspersed with a very small amount of amorphous structures in an aggregation state (FIG. 5D). While Aβ was incubated with H102 for 5 days, the formed Aβ fibrils are much less and thinner, with a diameter of about 3 to 6 nm and a length of 0.3 to 3 μm. The fibrils are woven into networks, interspersed with a very small amount of amorphous structures in an aggregation state (FIG. 5E). While Aβ was incubated with H103 for 5 days, Aβ fibrils are formed, with a diameter of about 5 to 8 nm and a length of about 0.5 to 5 μm. The fibrils are aggregated in a prick-type crystallization and woven into networks, interspersed with a small amount of amorphous structures in an aggregation state (FIG. 5F).

5. The effects of the polypeptides of the invention on the viability of SH-SY5Y cells.

Figure 6:
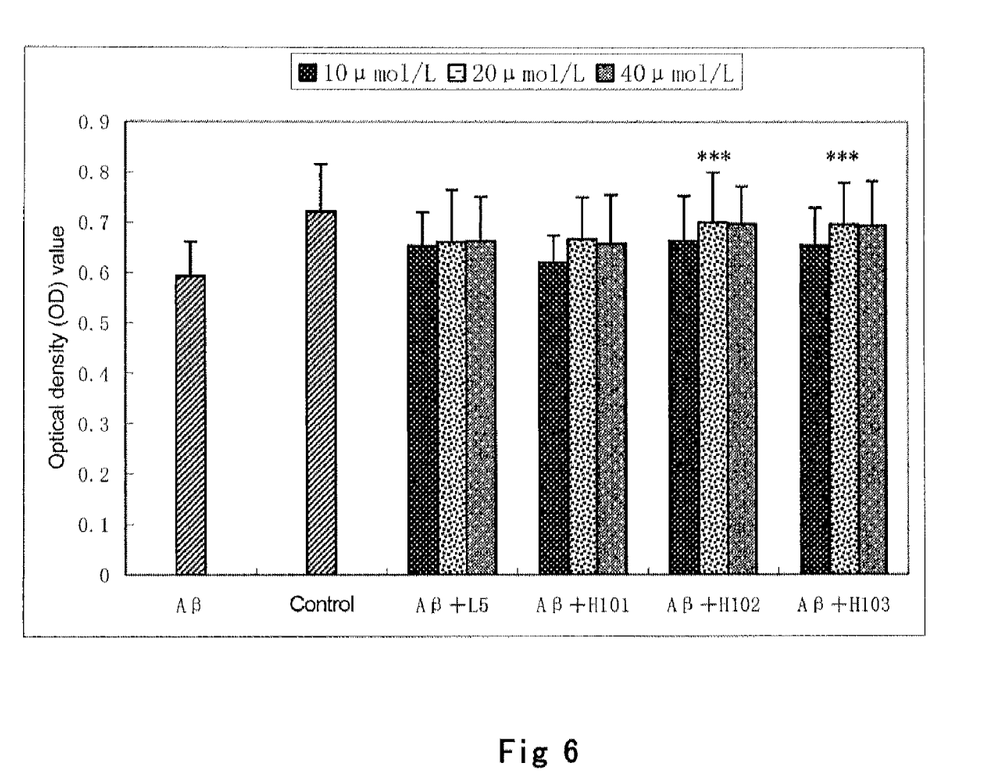
FIG. 6 shows the effects of various peptides at different concentrations (10 μmol/L, 20 μmol/L and 40 μmol/L) on the viability of human neuroblastoma cells SH-SY5Y which were incubated with $A\beta_{1-42}$ peptide of 5 μmol/L for 72 hours. n=12, * denotes P<0.05 as compared with the group of $A\beta_{1-42}$.
Figure 7A:
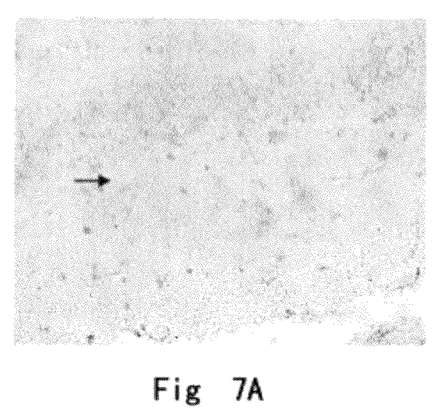
FIG. 7A: immunohistochemical staining results of mice from the control group, using the anti-APP N-terminal antibody.
Figure 7B:
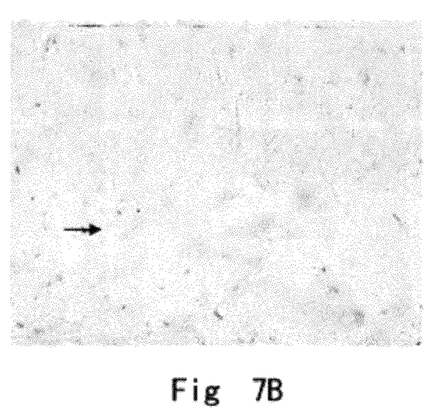
FIG. 7B: immunohistochemical staining results of mice from the control group, using the anti-Aβ antibody.
Figure 7C:
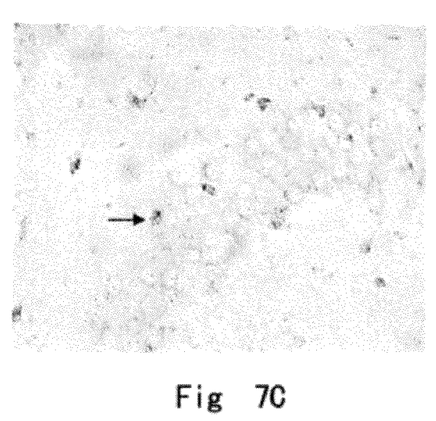
FIG. 7C: immunohistochemical staining results of mice from the model group, using the anti-APP N-terminal antibody.
Figure 7D:
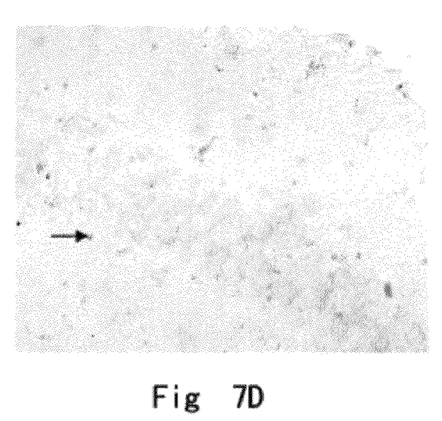
FIG. 7D: immunohistochemical staining results of mice from the model group, using the anti-Aβ antibody.
Figure 7E:
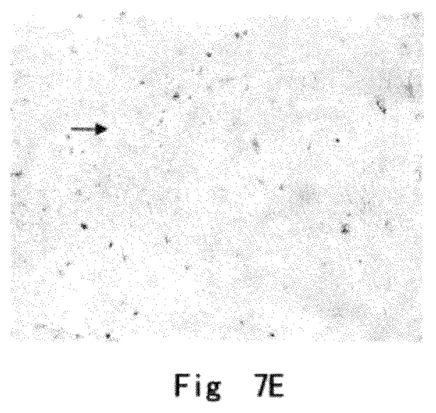
FIG. 7E: immunohistochemical staining results of mice from the injected group, using the anti-APP N-terminal antibody.
Figure 7F:
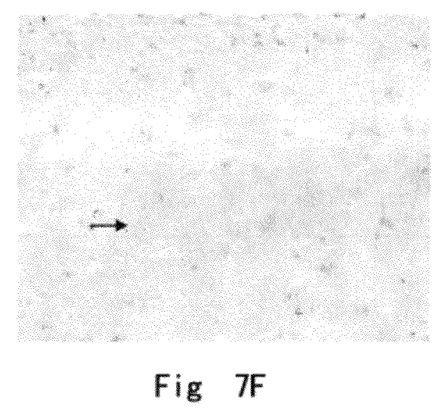
FIG. 7F: immunohistochemical staining results of mice from the injected group, using the anti-Aβ antibody.

FIG. 6 shows the effects of various peptides at different concentrations (10 μmol/L, 20 μmol/L and 40 μmol/L) on the viability of human neuroblastoma cells SH-SY5Y which were incubated with $Aβ_{1-42}$ peptide of 5 μmol/L for 72 hours. n=12, * denotes P<0.05 as compared with the group of $Aβ_{1-42}$.

As shown in FIG. 6, after incubation with $Aβ_{1-42}$ for 72 h, the viability of SH-SY5Y cells decrease. The addition of the four polypeptides at different concentrations (10 μmol/L, 20 μmol/L and 40 μmol/L) into the culture containing $Aβ_{1-42}$ improves the viability of cells, and the effect is dose-dependent. These results demonstrate that H102 is most effective to improve the viability of cells, and its optimal concentration is 20 μmol/L.

Example 3

The Effects of H102 on Gene Expressions of β-Amyloid (Aβ) and β-Amyloid Precursor Protein (APP) in the Brain of APP Transgenic Mice Materials and Methods Experimental animals: thirty APP 695 transgenic mice of nine-month-old and ten C57BL/6J mice which are matched in genetic background and age, were all purchased from experimental animal research center of Peking Union Medical College, Chinese Academy of Medical Sciences.

Reagents: anti-$Aβ_{1-42}$ antibody was purchased from Chemicon Inc. USA. Anti-APP antibody, Ready-to-use SABC Immunohistochemistry Staining Kit, DBA Color Development Kit, and Congo Red were purchased from Wuhan Boster Biological Technology, LTD. Other reagents were conventional reagents of analytic purity. The polypeptide H102 was synthesized, purified and identified as described in Example 1, and formulated into 40 μmol/L in normal saline for use in this experiment.

Animal grouping and model preparation: the thirty APP 695 transgenic mice were randomly divided into model group of 15 mice and the polypeptide-injected group of 15 mice. Ten C57BL/6J mice were used as a normal control group. For the polypeptide-injected group, the animals were received intracerebroventricular injection of 3 μl of saline solution containing H102 of 40 μmol/L each time. For the control group and model group, the animals were received intracerebroventricular injection of 3 μl of normal saline solution each time. The injection was carried out daily for 10 days. All animals were kept in the same conditions in SPF-grade mice room in the experimental animal research center of Tianjin Medical University The animals were anaesthetized intraperitoneally by 10% chloral hydrate at a dose of 400 mg/Kg weight. The animals were fixed on a brain stereotaxic frame, and the hair was cut off. After disinfection with Anerdian, the skin was incised along the midline of the head for about 1 cm. The periosteum was stripped to expose the bone marks. The head flat of the mouse was adjusted, such that Bregma and Lambda were at the same height. According to the George's brain stereotactic atlas, an aperture of 1 mm was made on the skull at the lateral ventricle ($P_{0.58}$, $R_1$, $H_{1.5}$) position for the needle entry. The injection was started on the second day after the surgery. With brain stereotaxic apparatus for small animals, 3 μl of solution of polypeptide or normal saline was slowly and steadily injected into the lateral ventricle by micro-injector. At the end of injection, the needle was kept in location for 1 min and then slowly withdrawn. The injected location then underwent the compression hemostasis. The injection was carried out daily for 10 days.

Preparation of paraffin sections of hippocampus of mice: after intracerebroventricular injections to animals of each group for 10 days, the animals were intraperitoneally anaesthetized by chloral hydrate of 0.1 kg/L at a dose of 4 mL/Kg weight. Rapid intubation was carried out via the left ventricle. In the meantime, the right atrium was incised, and saline was rapidly infused. When the liver became white, a paraformaldehyde solution of 40 g/L was infused instead, fast at first, then slowly, until the limbs of the mouse became rigid. The brain was removed and rapidly put into a paraformaldehyde solution containing 30% sucrose, fixed for 2 to 4 days. After the brain tissue sank, it was embedded in paraffin. The brain of mouse was sliced along the sagittal plane. When the hippocampal CA1 area was exposed, it was continuously sliced, and the samples were taken once every ten sections. For each mouse, three sections were taken for each antibody, with a thickness of 5 μm.

Immunohistochemical staining: according to the instructions of the immunohistochemistry kit, immunohistochemical staining was carried out against Aβ and APP, respectively. The dilution of the first antibody was 1:100 and 1:200, respectively, and dilution of the second antibody was 1:100. The stained sections were observed and imaged at 400× magnification.

Congo red staining of the mouse brain sections: the paraffin-embedded sections were immersed in ethanol-water mixture to de-wax (gradient: ethanol-water to water). The de-waxed sections were immersed in 10% paraformaldehyde solution for 15 min, and directly immersed in Congo red staining solution for 15 min. Then the sections were washed in water for 4 min, immersed in hematoxylin solution for 2 min, washed in water and immersed in 0.5% hydrochloric acid-ethanol solution for differentiation. The sections were fully washed in water to display blue color and then dehydrated by ethanol. Then they were transparentized by xylene and fixed by neutral gum. Finally, the stained sections were observed and imaged at 400× magnification.

Result

1. Immunohistochemical staining by Anti-APP N-terminal antibody and anti-Aβ antibody.

FIG. 7 shows the results of immunohistochemical staining of sections of hippocampal CA1 neurons of animals from each group by Anti-APP N-terminal antibody and anti-Aβ antibody.

As shown in FIG. 7, the results of immunohistochemical staining by Anti-APP N-terminal antibody and anti-Aβ antibody shows that: (1) the staining of hippocampal CA1 neurons of the control group is negative or weakly positive (FIG. 7A and FIG. 7B, respectively); (2) as compared with the control group, the samples of the model group have more positive cells, the expression is increased, and the staining is much deeper (FIG. 7C and FIG. 7D, respectively); and (3) as compared with the model group, the polypeptide injected group has less positive cells, the expression is decreased, and the staining is weaker (FIG. 7E and FIG. 7F respectively).

2. Congo Red Staining.

The mouse brain pathological sections were stained by Congo Red to observe amyloid plaque conditions in temporal cortex and hippocampus of mice. The results are shown in FIG. 8.

Figures 8A, 8B:
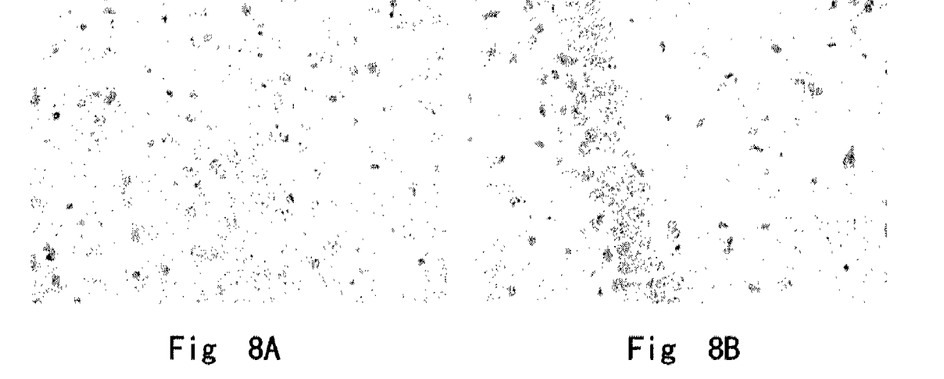
FIG. 8A: the Congo Red staining results of temporal cortex of mice from the control group.
FIG. 8B: the Congo Red staining results of hippocampus of mice from the control group.
Figures 8C, 8D:
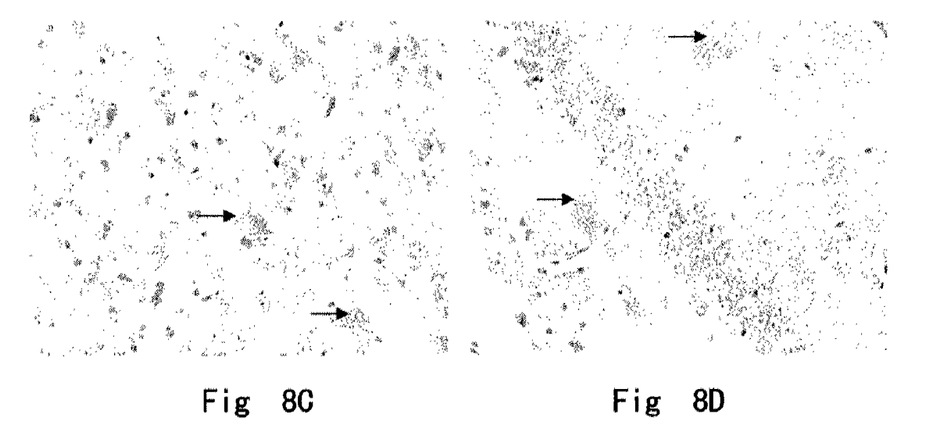
FIG. 8C: the Congo Red staining results of temporal cortex of mice from the model group.
FIG. 8D: the Congo Red staining results of hippocampus of mice from the model group.
Figures 8E, 8F:
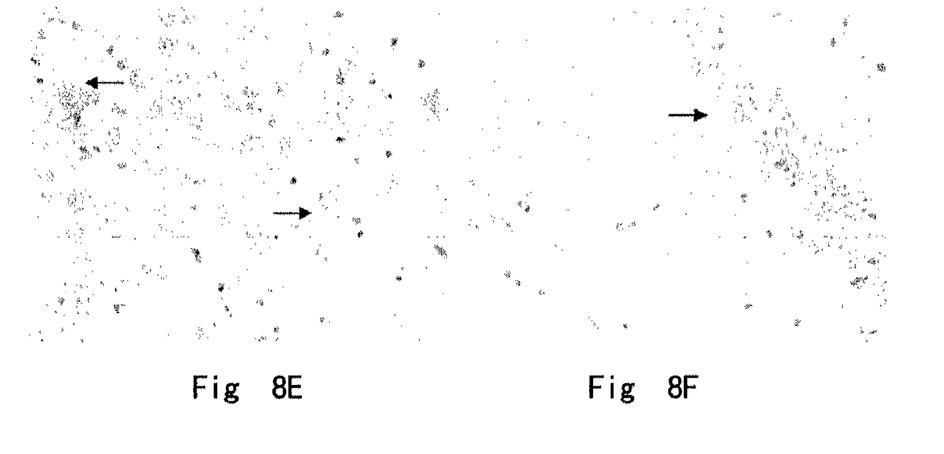
FIG. 8E: the Congo Red staining results of temporal cortex of mice from the injected group.
FIG. 8F: the Congo Red staining results of hippocampus of mice from the injected group.

As shown in FIG. 8: (1) there is no positive amyloid plaques in temporal cortex (FIG. 8A) and hippocampus (FIG. 8B) of mice in the control group; (2) in temporal cortex (FIG. 8C) and hippocampus (FIG. 8D) of mice in the model group, there are large or small, pale red colored clumping amyloid plaques, which are mostly round or oval in shape, scattered at a uneven distribution, and surrounded by more or less neurons; and (3) in temporal cortex (FIG. 8E) and hippocampus (FIG. 8F) of mice in the polypeptide injected group, there are also some clumping amyloid plaques, but the number of amyloid plaques in the polypeptide injected group is obviously lower than that of the model group.

Conclusions

Immunohistochemical staining shows that, in brain CA1 area of the model mice, the amount of $A\beta_{1-42}$ positive cells is much higher than that of the normal control group. Whereas the amount of $A\beta_{1-42}$ positive cells in the H102 polypeptide injected group is much lower than that of the model group. Thus, it is inferred that H102 can inhibit Aβ aggregation and reduce the toxicity of Aβ in vivo. In addition, Congo red staining shows that amyloid plaques clearly form in brain of the transgenic mice, and do not form in normal control mice; whereas the amyloid plaques formed in H102 polypeptide injected mice are much lower in the number and size than that in the transgenic group. These results confirm that H102 can reduce the Aβ generation and inhibit its aggregation.

In the present application, a variety of publications are cited, which are incorporated herein by their entirety by reference, in order to describe the state of the art to which the invention pertains in more detail.

It is apparent to the person skilled in the art that various modifications and changes can be made to the invention without departing the spirits and scopes thereof. Other embodiments of the invention are apparent to the person skilled in the art by considering the descriptions and examples disclosed herein. The descriptions and examples disclosed herein are intended to be interpreted as only exemplary and the actual scopes and spirits of the invention are defined in the attached claims.

The invention claimed is:

1. A purified polypeptide comprising the amino acid sequence of His-Lys-Gln-Leu-Val-Phe-Phe-Glu-Glu-Asp (SEQ ID NO: 1).

2. A purified polypeptide comprising the amino acid sequence of

His-Lys-Gln-Leu-Pro-Phe-Phe-Glu-Glu-Asp. (SEQ ID NO: 2)

3. A pharmaceutical composition comprising the polypeptide of claim 1 and a pharmaceutically acceptable carrier.

4. A method for treatment of Alzheimer's Disease in a subject, comprising administering an effective amount of the polypeptide of claim 1 to the subject.

5. A pharmaceutical composition comprising the purified polypeptide of claim 2 and a pharmaceutically acceptable carrier.

6. A method for treatment of Alzheimer's Disease in a subject, comprising administering an effective amount of the polypeptide of claim 2 to the subject.

* * * * *